(12) United States Patent
Fecteau et al.

(10) Patent No.: US 12,178,584 B2
(45) Date of Patent: Dec. 31, 2024

(54) COMPUTER-IMPLEMENTED METHOD OF HANDLING ELECTROCARDIOGRAM DATA

(71) Applicant: ICENTIA INC., Québec (CA)

(72) Inventors: Pierre Fecteau, St-Augustin-de-Desmaures (CA); Germain Éthier, Québec (CA)

(73) Assignee: ICENTIA INC., Québec (CA)

( * ) Notice: Subject to any disclaimer, the term of this patent is extended or adjusted under 35 U.S.C. 154(b) by 627 days.

(21) Appl. No.: 17/235,113

(22) Filed: Apr. 20, 2021

(65) Prior Publication Data

US 2021/0236040 A1    Aug. 5, 2021

Related U.S. Application Data

(63) Continuation of application No. 16/338,573, filed as application No. PCT/CA2017/051310 on Nov. 3, 2017, now Pat. No. 11,006,884.

(60) Provisional application No. 62/417,712, filed on Nov. 4, 2016.

(51) Int. Cl.
| | |
|---|---|
| *A61B 5/339* | (2021.01) |
| *A61B 5/024* | (2006.01) |
| *A61B 5/349* | (2021.01) |
| *A61B 5/352* | (2021.01) |
| *G16H 10/60* | (2018.01) |
| *G16H 50/20* | (2018.01) |

(52) U.S. Cl.
CPC ............. *A61B 5/339* (2021.01); *A61B 5/349* (2021.01); *A61B 5/352* (2021.01); *G16H 10/60* (2018.01); *G16H 50/20* (2018.01); *A61B 5/024* (2013.01)

(58) Field of Classification Search
CPC ........ G16H 10/60; G16H 50/20; A61B 5/024; A61B 5/7485; A61B 5/346
See application file for complete search history.

(56) References Cited

U.S. PATENT DOCUMENTS

| | | | |
|---|---|---|---|
| 6,409,659 B1 | 6/2002 | Warner et al. |
| 7,819,813 B2 | 10/2010 | Nagai et al. |
| 8,983,584 B2 | 3/2015 | Moorman et al. |
| 9,918,651 B2 | 3/2018 | Borjigin et al. |
| 2005/0222510 A1 | 10/2005 | Hadley |
| 2013/0109988 A1 | 5/2013 | Kim et al. |
| 2016/0015313 A1 | 1/2016 | Sugarman et al. |
| 2016/0192850 A1 | 7/2016 | Gregg |

(Continued)

FOREIGN PATENT DOCUMENTS

| | | |
|---|---|---|
| CN | 104173046 A | 12/2014 |
| JP | 04150832 A | 5/1992 |
| JP | 05176906 A | 7/1993 |

(Continued)

OTHER PUBLICATIONS

Fratini et. al., "Individual identification via electrocardiogram analysis"; School of Life and Health Sciences, Aston University, Aston Triangle, B4, 7ET Birmingham, UK; vol. 14; Art: 78 (2015); pp. 1-23.

(Continued)

*Primary Examiner* — Paula J Stice
(74) *Attorney, Agent, or Firm* — Reno Lessard; Norton Rose Fulbright Canada LLP

(57) ABSTRACT

This specification describes a method of visually displaying electrocardiogram data in a compressed manner on the display screen wherein rhythmic information is visible and a method of categorizing zones of the electrocardiogram data.

12 Claims, 6 Drawing Sheets

(56) References Cited

U.S. PATENT DOCUMENTS

2016/0213333 A1    7/2016  Guerrero

FOREIGN PATENT DOCUMENTS

| JP | 2002253515 A | 9/2002 |
| JP | 2004167006 A | 6/2004 |
| WO | 201036805 A1 | 3/2016 |

OTHER PUBLICATIONS

Warner, R.A. et al, "Marquette Waterfall Display", GE Healthcare, Apr. 2002, General Electric Company, U.S.A.

"Schiller's Medilog Holter system", Schiller the Art of Diagnostics, 2013, Switzerland.

Williamson, C.A. et al., "Sensitivity of Compressed Spectral Arrays for Detecting Seizures in Acutely Ill Adults", Neurocrit Care, vol. 20, Issue 1, p. 32-39, Sep. 20, 2013.

Al-Ziarjawey H.A.J. et al., "Heart Rate Monitoring and PQRST Detection Based on Graphical User Interface with Matlab", International Journal of Information and Electronics Engineering, vol. 5, No. 4, p. 311-316, Jul. 31, 2015.

Sabarimalai et al., "An Efficient R-peak Detection Based on New Nonlinear Transformation and First-Order Gaussian Differentiator", Cardiovascular Engineering and Technology, vol. 2, No. 4, Dec. 2011.

Kawther Soualhi et Al: "ECG Image Representation of Normal Sinus Rythm", 2014, Tunisia, 1st International Conference on Advanced Technologies for Signal and Image Processing (ATSIP), IEEE, Mar. 17, 2014, pp. 225-230, XP032606058.

Gang Zheng et Al: "Study of Human Identification by Electrocardiogram Waveform Morph", Dec. 3, 2011, International Conference of Financial Cryptography and Data Security; Springer-Verlag, Berlin, Heidelberg, LNCS 7098, pp. 269-278, XP047439265.

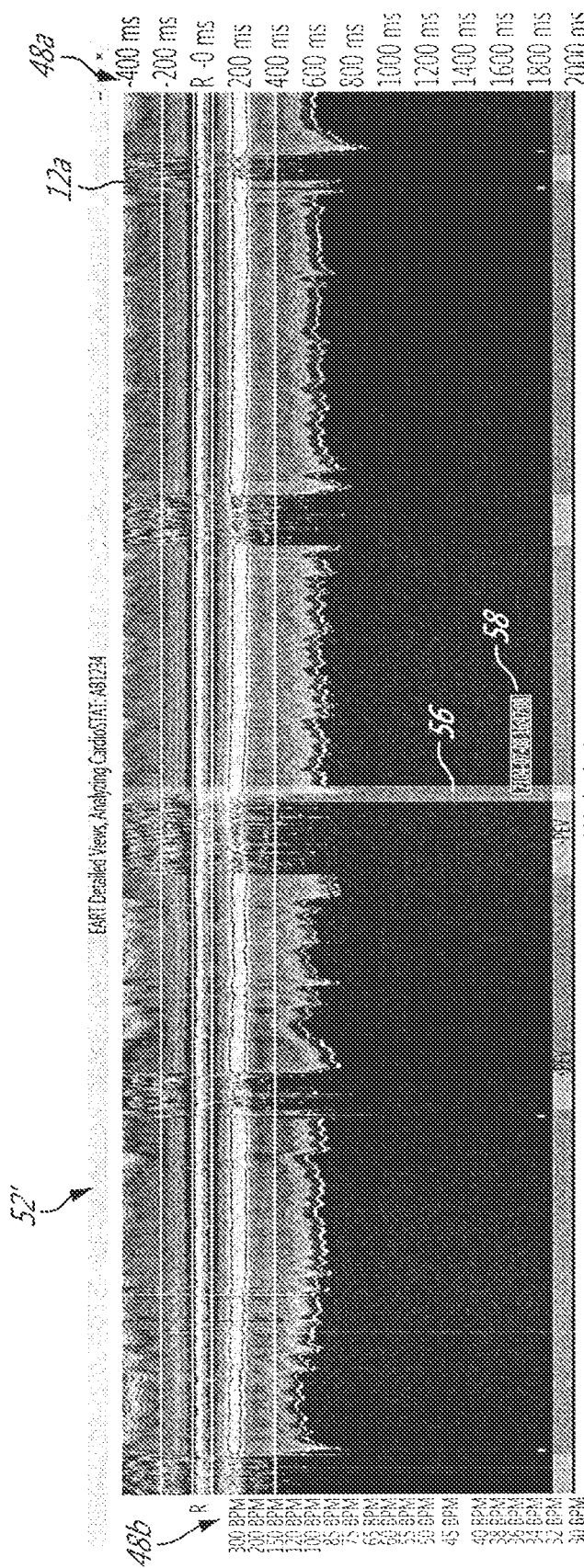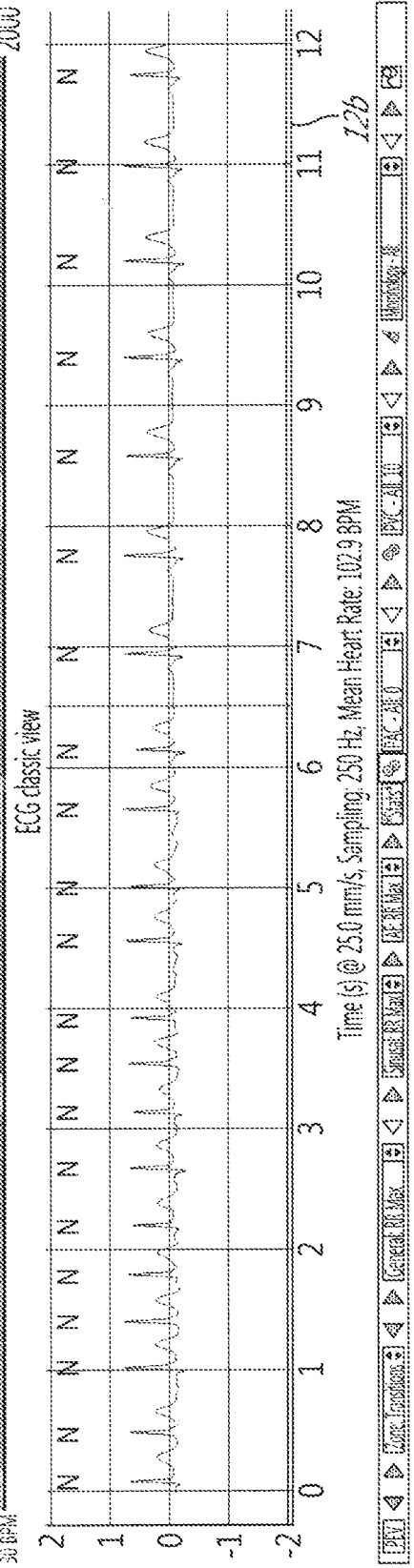
FIG. 4

COMPUTER-IMPLEMENTED METHOD OF HANDLING ELECTROCARDIOGRAM DATA

BACKGROUND

Electrocardiography (ECG) is the process of recording the electrical activity of the heart over a period of time, and is typically performed by applying electrodes to the patient's skin. Computerized electrocardiography produces electrocardiogram data having magnitude values of the recorded electrical activity varying over time. Electrocardiogram data can include absolute time values associated with each one of the magnitude values. Alternately, the time reference can be implicit. For instance, if the period of time elapsed between successive ones of the magnitude values is constant and known, it may not be necessary to store an absolute value of time for every magnitude value to be able to reconstruct and display the electrocardiogram.

For decades, electrocardiograms were printed directly on a paper sheet in the form of a two-dimensional graph having the magnitude plotted along the Y-axis and the time plotted along the X-axis. FIG. 1A illustrates a given period of time of an electrocardiogram presented with this method, and includes a first heartbeat 10 and the beginning of a second heartbeat 10'. A consecutive sequence of normal heartbeats are referred to as normal sinus rhythm and have reference features which are recognizable. The exact expression of these recognizable features can vary significantly from one heartbeat to another, from one person to another, and can also depend on the recording method, but are typically present in one form or another. These recognizable features include "peaks" referred to as P, Q, R, S and T peaks in the art.

In the context where normal resting heart rate typically ranges between 60 and 100 beats per minute, it will be understood from looking at FIG. 1A that electrocardiograms spanning any significant amount of time can require an imposing amount of paper.

In recent years, it has become increasingly common to store electrocardiogram data in a memory readable by a computer, and to display the electrocardiogram data on a computer display screen rather than print it on paper. Typically, only a relatively small portion of the electrocardiogram data is displayed at any given time, and a user can navigate the electrocardiogram data by providing inputs which are used as commands to change the displayed portion of the electrocardiogram data.

There was a need for displaying larger periods of time of electrocardiogram data at once on the display screen, e.g. minutes of electrocardiogram data. This need was met to a certain extent by a new method of displaying electrocardiogram data which has been published in recent years. This new method involved compressing the displayed data by using a color scale to plot magnitude rather than by using the Y-axis of the 2D graph. Accordingly, the display of the electrocardiogram data could be compressed to a single axis. Moreover, algorithms have been developed to recognize individual heartbeats automatically in the electrocardiogram data. Accordingly, single-axis graphs could be displayed for corresponding heartbeats. By orienting the single-axis graphs transversally and displaying them side-by-side, an impressive amount of heartbeats could be displayed on the display screen all at once.

While former technologies were satisfactory to a certain degree, there remained room for improvement in terms of displaying, navigating, annotating, and otherwise handling the electrocardiogram data using a computer.

SUMMARY

In accordance with one aspect, there is provided a method of displaying electrocardiogram data on a display screen of a computer, the electrocardiogram data having a collection of magnitude values varying over time and representing a succession of heartbeats, the method comprising: the computer displaying the electrocardiogram data within an elongated rectangular portion of the display screen, with a plurality of single axis graphs extending transversally relative to the length of the rectangular portion, and positioned immediately adjacent to one another along the length of the rectangular portion, each graph in the sequence representing a corresponding, successive, period of time of the electrocardiogram data with the magnitude values displayed by corresponding colors or tones as a function of a color and/or tone magnitude scale, and corresponding time values plotted along the single axis, wherein heartbeats represented by corresponding ones of the graphs each have a common alignment reference feature being transversally aligned with a common transversal reference coordinate of the rectangular portion, and ending at a common rhythmic reference feature, the transversal positions of the ends of the graphs varying from one graph to another as a function of heartbeat rhythm; and the computer further displaying a remaining area extending transversally between the ends of the graphs and a corresponding edge of the rectangular portion in a manner contrasting with the color and/or tone scale of the graphs.

In accordance with another aspect, there is provided a computer-implemented method of handling electrocardiogram data, the method comprising: the computer displaying the electrocardiogram data on a display screen, the displayed electrocardiogram data having a plurality of magnitude values varying over time and representing a succession of heartbeats; the computer categorizing a zone of the electrocardiogram data including: receiving a first user input and identifying a first temporal coordinate of the electrocardiogram data based on the first user input; receiving a second user input and identifying a second temporal coordinate of the electrocardiogram data based on a second user input; defining the zone of the electrocardiogram data as extending between the first temporal coordinate and the second temporal coordinate; receiving a third user input and associating a category with the defined zone based on the third user input.

Many further features and combinations thereof concerning the present improvements will appear to those skilled in the art following a reading of the instant disclosure.

It will be understood that the expression "computer" as used herein is not to be interpreted in a limiting manner. It is rather used in a broad sense to generally refer to the combination of some form of one or more processing units and some form of memory system accessible by the processing unit(s). A computer can be a personal computer, a smart phone, a tablet, an appliance computer, etc.

It will be understood that the various functions of the computer, or more specifically of the processing unit or of the memory controller, can be performed by hardware, by software, or by a combination of both. For example, hardware can include logic gates included as part of a silicon chip of the processor. Software can be in the form of data such as computer-readable instructions stored in the memory system. With respect to a computer, a processing unit, a memory controller, or a processor chip, the expression "configured to" relates to the presence of hardware, software, or a combination of hardware and software which is operable to perform the associated functions.

DESCRIPTION OF THE FIGURES

In the figures,

FIG. 4 shows an example of the graphical representation of FIG. 2 applied to an upper portion of a display screen;

DETAILED DESCRIPTION

Figure 2:
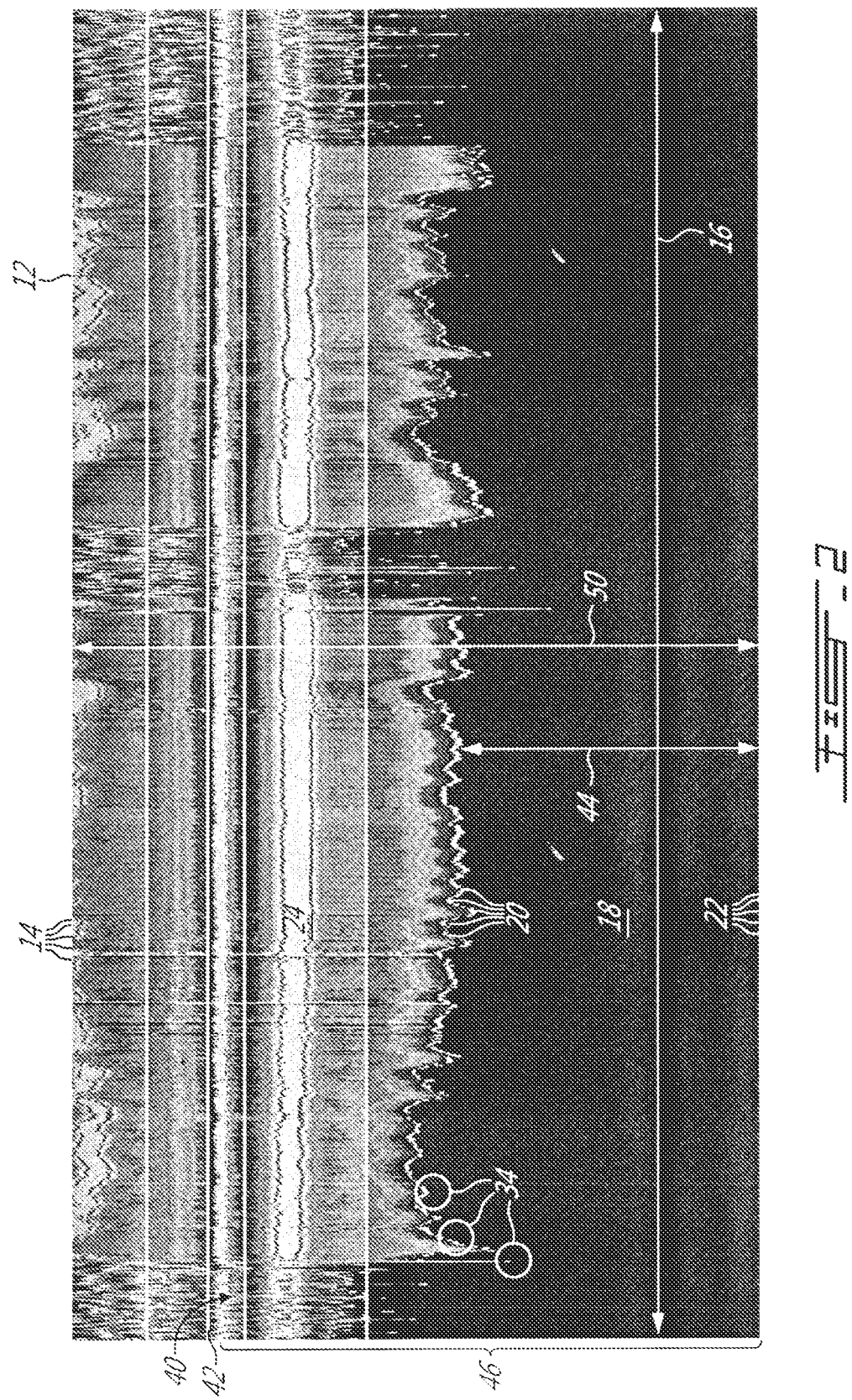
FIG. 2 is a rectangular portion of a display screen in which a plurality of single axis graphs such as shown in FIG. 1A are disposed side-by-side in succession, in accordance with an embodiment.

Referring to FIG. 2, an example of electrocardiogram data graphically represented on a rectangular portion 12 of a display screen is shown. In this embodiment, individual single-axis graphs 14 are displayed adjacent to one another along a length 16 of the rectangular portion 12. The individual single axis graphs 14 are aligned transversally to the length 16 of the rectangular portion 12, and each represents a plurality of magnitude values by a color and/or tone scale, and associated time values as spatial coordinates along the single axis. The rectangular portion 12 of the display screen typically exceeds the duration of the individual graphs, and a remaining area 18 extending between ends 20 of the graphs 14 and a corresponding edge 22 of the rectangular portion 12 is displayed in a manner to visually contrast with the color and/or tone scale used in the graphs 14. As will be detailed below, this remaining area 18, combined with the method of graphically representing the individual heartbeats of the electrocardiogram data, allows to display rhythmic (heartbeat frequency) information to the skilled user in addition to the magnitude values of a given heartbeat. The exact color and/or tone scale can be selected as a function of a specific application, and can alternately be made adjustable by the user. It was found that at least in some embodiments, it could be advantageous that the color and/or tone scale have contrast in a thickness zone 24 of T wave. The displayed electrocardiogram data can have been previously obtained in any suitable manner, including by a fixed electrocardiography recording device, and wearable electrocardiography recording devices such as traditional Holter monitors and more recent technology such as the CardioSTAT® device manufactured by Icentia Inc. Pre-treatment can be made on the electrocardiogram data prior to displaying it, such as automatic recognition of the heartbeats. Wearable monitors such as the CardioSTAT® device can pose a particular challenge when they are designed to record electrocardiogram data over a relatively long period of time, e.g. more than a few minutes, typically more than a few hours, and preferably several days or more. Such an enormous amount of resulting data cannot be processed in a traditional manner. As will be seen below, software can be provided to allow addressing such amounts of data using a computer, and which can allow the user to navigate quickly across the data in relatively large time increments, such as minutes or even hours.

In the embodiment illustrated, automatic heartbeat recognition is performed via a QRS complex detection algorithm based on a paper entitled "An Efficient R-Peak Detection Based on New Nonlinear Transformation and First-Order Gaussian Differentiator" authored by P. Kathirvel et al and published online on Oct. 12, 2011 in Cardiovascular Engineering and Technology, Vol. 2, No. 4, December 2011, pp. 408-425. It generally involved the steps of:

bandpass filtering the ECG signal, between 0.5 Hz and 40 Hz;
non-linear transformation consisting of raising to the power of 2 each sample while preserving its sign;
amplitude estimation using a regressive low pass filter;
addition of a high frequency component scaled by the amplitude estimation;
determining the number zero-crossing events; and
R-peak detection by applying a threshold to the zero-crossing counts.

Figure 1:
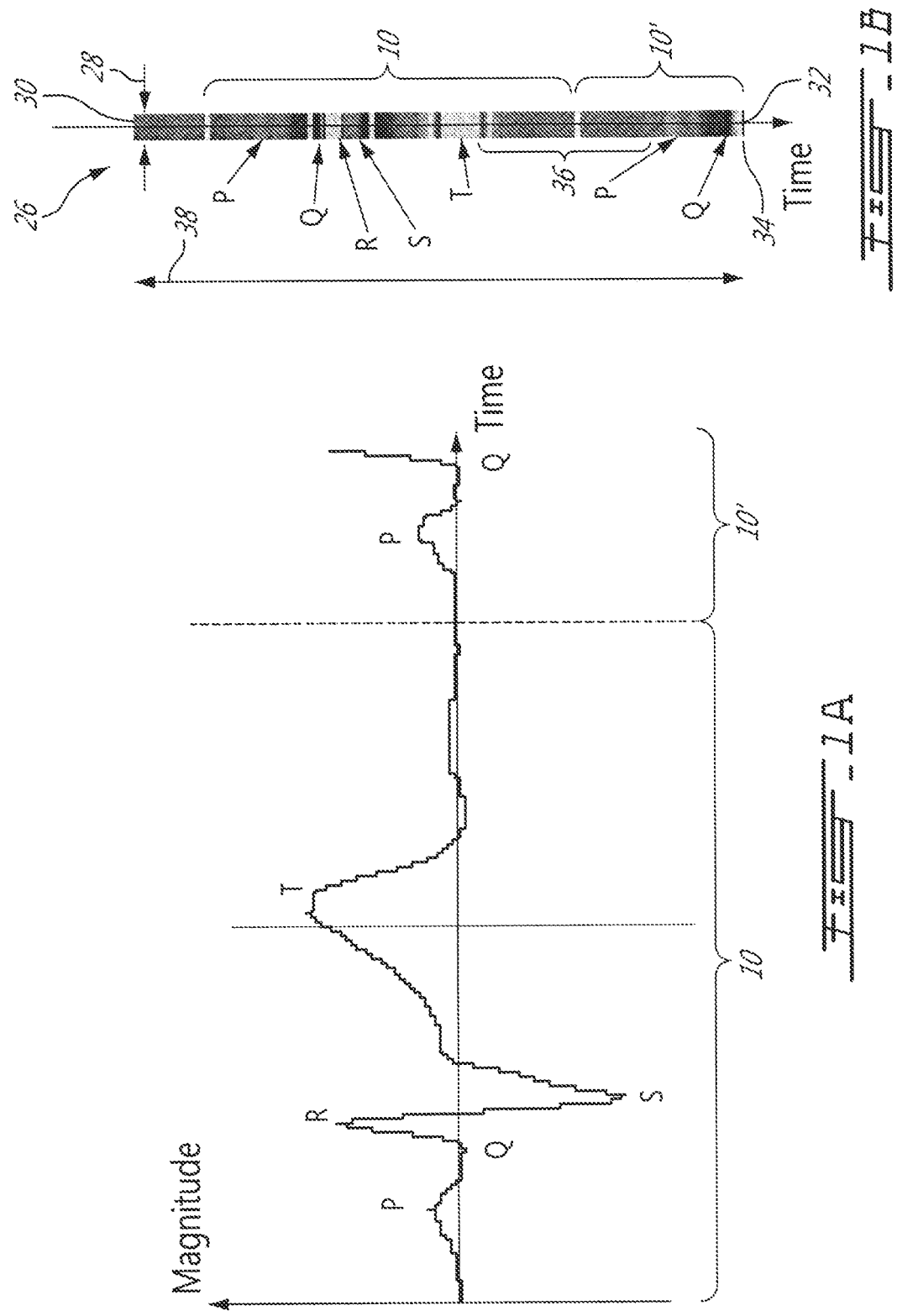
FIG. 1A is a portion of a two-dimensional graph representing electrocardiogram data with time coordinates plotted on an X-axis and corresponding amplitude coordinates plotted on a Y-axis.
FIG. 1B is an example of a unidimensional (single-axis) graph representing the electrocardiogram data which substitute a color and/or tone scale to the Y-axis of the graph of FIG. 1B, the width of the single axis graph is enlarged to facilitate its illustration.

Referring to FIG. 1B, an example of an individual single-axis graph 26 representing a portion of electrocardiogram data having a normal sinus rhythm is shown. The individual single-axis graph 26 shown in FIG. 1B has its width 28 enlarged to facilitate illustration. In practice, there is a motivation to reduce its width 28 as much as possible, ideally to a single pixel, and to position the individual graphs immediately adjacent to one another, into a graphical representation such as shown in FIG. 2, as this can allow compressing more data into the area of the rectangular portion 12 of the display screen. In practice, it can nonetheless be required to use more than a single pixel to represent the width 28 of the individual graphs. On the other hand, instead of displaying all the heartbeats, some graphs can be skipped to further compress the data. For instance, only one graph for each group of a given number of adjacent heartbeats can be displayed, such as one in three, or one in five, for instance. The temporal coordinates spanning the single axis extend from an upper portion 30 of the graph 26 to a lower portion 32 of the graph 26 in this embodiment. It will be seen that in this embodiment, the graph 26 does not only include the electrocardiogram data corresponding to a corresponding heartbeat 10 (the first P, Q, R, S and T peaks extending from the upper portion of the graph towards the lower end thereof), but further extends to a common rhythmic reference feature 34.

The rhythmic reference feature 34 can vary from one embodiment to another, but will typically be the same (common) for a given instance of plurality of graphs 14 being displayed simultaneously, adjacent one another such as shown in FIG. 2, in a manner to display rhythmic information to the user in an intuitive manner. The common rhythmic reference feature 34 can be associated with a Q peak, a R peak or a S peak of a next heartbeat 10', for instance. The common rhythmic reference feature 34 can be automatically identified by the computer, via an algorithm, as will be exemplified below. In the embodiment shown in FIG. 1B, the common rhythmic reference feature 34 was selected to be the beginning of the R peak of the next heartbeat 10'. Accordingly, the graph 26 can be seen to further extend along the P peak and the Q peak of the next heartbeat 10', and to include the duration of the pause 36 between the T peak of the corresponding heartbeat 10 and the P peak of the next heartbeat 10'. Accordingly, the single axis graph 26 ends at the common rhythmic reference feature 34 and the length 38 of the graph 26 can vary depending on the heartbeat rate and on the duration of the pause 36, for instance.

To construct the graphical representation of FIG. 2, another common reference feature of the individual heartbeats is detected and used to transversally align the graphs 14 relative to one another. This latter common reference feature will be referred to as the common alignment reference feature 40. The common alignment reference feature 40 can vary from one embodiment to another, but will typically be the same (common) for a given instance of a plurality of graphs 14 being simultaneously displayed adjacent one another, and can be selected to be the same reference feature than the common rhythmic reference feature 34, in a manner to display rhythmic information to the user in an intuitive manner. Each one of the graphs 14 in the rectangular portion 12 of the display screen can be transversally-aligned with the others by positioning its detected common alignment reference feature 40 at a common transversal alignment coordinate 42 of the rectangular portion 12.

In the embodiment displayed in FIG. 2, the common alignment reference feature 40 is the beginning of the R peak of the corresponding heartbeat, and a period of time between the beginning of the R peak of the corresponding heartbeats and the beginning of the R peak of the next heartbeat, which is representative of heartbeat rate, is graphically displayed in the form of a length of a portion of the single axis graph which extends from the common transversal alignment coordinate 42 of the rectangular portion 12 to the end of the graph 20 (the end 20 associated with the common rhythmic reference feature 34), in the direction of a corresponding edge 22 of the rectangular portion 12. Accordingly, the transversal coordinate of the end of a given one of the graphs 14 can be correlated to an instantaneous heartbeat rate between the corresponding heartbeat and the next heartbeat, or conversely, to an amount of time between the corresponding heartbeat and the next heartbeat. The transversal coordinates of the ends 20 of the graphs 14 can be made easily visible to a user by displaying the portion of the rectangular portion 12 which immediately follows the ends 20 in a color and/or tone which contrast sharply with the color and/or tone scale of the graphs 14, and more specifically with a typical color and/or tone of the common rhythmic reference feature 34. In FIG. 2, for instance, the beginning of the R peak typically has an amplitude represented in white on the color and/or tone scale, and the remaining area 18 of the rectangular portion 12 exceeding the ends 20 of the graphs 14 is entirely left black. More generally, the remaining area 18 can be represented in a color and/or tone scale which contrast with the color and/or tone scale used to display the magnitude of the electrocardiogram data in the graphs 14. In the specific embodiment illustrated, "warm" colors leading to white, passing by yellow and red, are used to represent increasing positive amplitudes, whereas "cold" colors leading to dark blue are used to represent negative amplitudes.

Still referring to FIG. 2, the graphs 14 in this embodiment are positioned immediately adjacent to one another along the length 16 of the rectangular portion 12. Each graph 14 in the sequence represents a corresponding, successive, period of time of the electrocardiogram data with the magnitude values displayed by corresponding colors or tones as a function of a color and/or tone magnitude scale. The time values associated with the magnitude values are plotted along the single axis. The heartbeats represented by corresponding ones of the graphs 14 each have a common alignment reference feature 40 being transversally aligned with a common transversal reference coordinate 42 of the rectangular portion 12. The graphs 14 end at a common rhythmic reference feature 34. The transversal positions of the ends 20 of the graphs 14 vary from one graph 14 to another as a function of heartbeat rhythm which, in combination with the contrasting remaining area 18 of the rectangular portion 12, forms a margin 44 extending along a corresponding edge of the rectangular portion 12. The margin 44 varies in thickness along the length 16 of the rectangular portion 12 as a function of heartbeat rhythm.

The transversal coordinates of the edge 22 of the rectangular portion 12 which corresponds to an edge of the margin 44 can be correlated to a given time interval 46 since the common alignment reference feature 40, and thus be at a given, constant, spatial distance from the common transversal alignment coordinate 42. This time interval 46 can be associated with a maximum time interval allowed by the dimensions of the rectangular portion 12 of the display screen and the display configuration. This time interval 46 will typically be selected in a manner to be sufficient to encompass the maximum possible time interval which can normally be expected between heartbeats. In this embodiment, it was selected to be of 2 seconds based on the beginning of the R-peak, the common rhythmic reference feature 34. In other embodiments, the time interval 46 can be of more than 1.4 second, or more than 1.8 second, for instance. In still other embodiments, the time interval 46 can be made adjustable based on a user input, for instance. The scale of the time interval 46 can be displayed adjacent to the rectangular portion 12, to facilitate analysis by a user, such as shown in FIG. 4, for instance, where the time interval 46 is presented in a time scale 48$a$ having units of milliseconds on the right-hand side of the display. Conversely, the time interval 46 can be indicative of heart rate, and a heart rate scale 48$b$ can be displayed adjacent to the rectangular portion 12. For instance, in FIG. 4, the heart rate scale 48$b$ in beats per minute (BPM) is presented on the left-hand side of the display.

Figure 3:
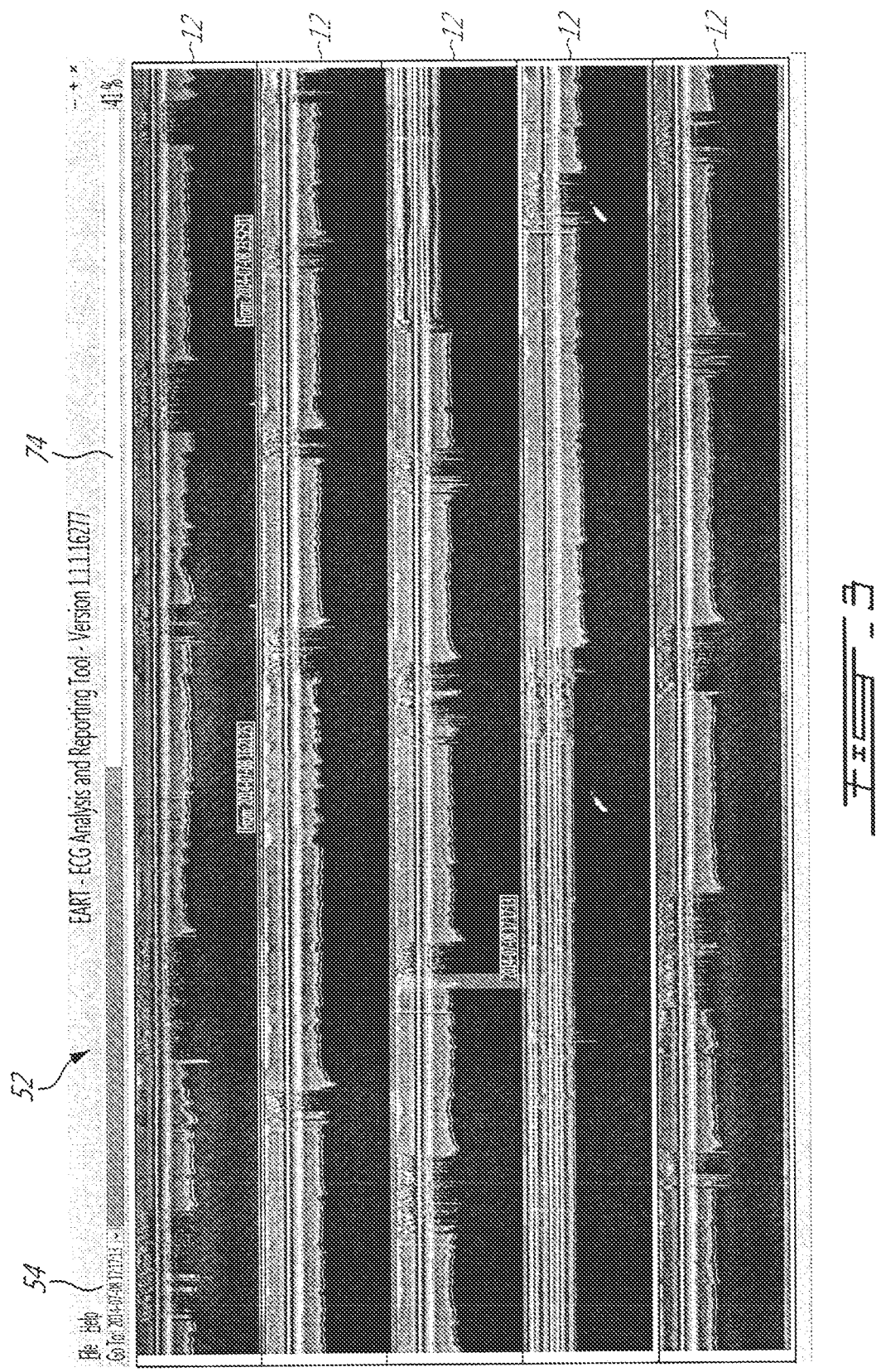
FIG. 3 shows an example of the graphical representation of FIG. 2 applied to several superposed rows of a display screen.

There can be an incentive to reduce the transversal width 50 of the rectangular portion 12, as this can allow to include more rows of electrocardiogram data, and thus more electrocardiogram data displayed simultaneously at a given time on a given screen, in a display configuration such as shown in FIG. 3. To this end, it can be preferred in an alternate embodiment to use a shorter time interval 46, or to use a logarithmic scale instead of the linear scale used in the illustrated figures. In an embodiment using a logarithmic scale, numerical values associated with the logarithmic scale can be displayed adjacent the display, for instance.

In electrocardiogram data, there may be events where a pause between a first heartbeat 10 and a second heartbeat 10' exceeds the time interval 46. This can be dealt with in various manners. In the illustrated embodiment, if the pause exceeds the time interval 46, the graph of the first heartbeat 10 is continued until the edge of the rectangular portion 12, which creates a transversal line extending fully across the rectangular portion 12 and makes the event very easy to detect by a trained technician consulting the displayed electrocardiogram data. Moreover, if the pause lasts for even more units of the time interval 46, subsequent graphs can be displayed with the electrocardiogram data corresponding to the different time interval units of the pause following the first heartbeat 10. This can broaden, in the direction of the length 16 of the rectangular portion 12 the thickness of the transversal line extending fully across the rectangular portion 12, and can provide a very intuitive indication of the length of the pause to a skilled technician or to a physician consulting the displayed electrocardiogram data. The second (subsequent) heartbeat 10', when it comes, can then be normally displayed, with its common alignment reference feature 40 aligned with the common transversal alignment coordinate 42.

In other words, the electrocardiogram data can be displayed based on the following conditions:
- if a heartbeat 10 is associated with the period of time corresponding to a given graph, the magnitude values spanning P, Q, R, S and T peaks of the associated heartbeat are displayed in the given graph;
- if a heartbeat 10 is associated with the period of time corresponding to a given graph and a next heartbeat 10' is further associated with a next period of time of the electrocardiogram data, the magnitude values spanning from the T peak of the associated heartbeat 10 to the common rhythmic reference feature 34 of the next heartbeat 10' are displayed in the given graph, including at least a P peak of the next heartbeat 10';
- if a heartbeat 10 is associated with the period of time corresponding to a given graph and a next heartbeat 10' is not associated with a next period of time of the electrocardiogram data, magnitude values spanning from the T peak of the associated heartbeat to a maximum duration of the given graph are displayed in the given graph, (the maximum duration of the given graph corresponds to the spatial coordinates of the corresponding edge 22 of the rectangular portion 12); and
- if a heartbeat 10 is not associated with the period of time corresponding to a given graph, magnitude values spanning the entire duration of the period of time are displayed in the given graph, leading to the maximum duration.

In a display configuration 52 such as shown in FIG. 3, the time coordinates of the electrocardiogram data can progress from left to right, and then continue on the left side of a lower one of the rectangular portions 12, and so forth. Moreover, the application responsible for displaying the electrocardiogram data can include, within its user interface, means for the user to easily navigate the electrocardiogram data (to move along the electrocardiogram data and successively show new portions of the electrocardiogram data while hiding previously displayed portions of the electrocardiogram data). In this embodiment, using the down key on a keyboard can allow the user to navigate the rectangular portions 12 forming the rows of the display by moving "down" one row at a time, for instance, whereas keys such as the page down and page up keys can allow to navigate by the entire amount of displayed rows (5 in this case) at a single time. As shown in FIG. 3, in this embodiment, a "Go To" area 54 of the graphical interface is displayed in an upper left corner of the screen. By activating the "Go To" area 54 of the graphical interface, a user can access a calendar, and select a specific day in the calendar corresponding to the portion of the electrocardiogram data that the user wishes to see displayed. Additional keys, such as a home key or an end key, for instance, can be used as user inputs to allow a user to navigate directly to the beginning period, or the final period, of the electrocardiogram data, for instance.

FIG. 4 shows another example display configuration 52'. In FIG. 4, compressed electrocardiogram data is displayed as presented above in a first rectangular portion 12a of the display screen, whereas a portion of the electrocardiogram data displayed in the first rectangular portion 12a is displayed, using a "classic" two-dimensional representation, in a second rectangular portion 12b of the display screen. In this embodiment, the application displaying the electrocardiogram data can further be configured to be able to receive a user input indicating spatial coordinates corresponding to at least one of the single axis graphs displayed in the first rectangular portion 12a, and to display, in the second rectangular portion 12b, the two-dimensional representation of the portion of the electrocardiogram data which was selected via the user input. The user input can be received by a user left-clicking a corresponding portion of the first rectangular portion 12a, or the corresponding portion on the screen, for instance. A visual indicator 56 can be displayed on the first rectangular portion 12a to indicate which portion of the electrocardiogram data is being displayed in the second rectangular portion 12b of the display screen. In this embodiment, the visual indicator is a vertical column of shading or highlighting. If two screens are used, the display of FIG. 4 can be presented on a first display screen, and the display of FIG. 3 can be displayed on a second display screen. The two display screens can be linked in a manner that navigating to a new position on any one of the rectangular portions can automatically trigger the adjustment of the position of the marker on the other graphical representations. For instance, a visual indicator can also be presented at a corresponding area of the second display screen. In this embodiment, a transversal line is used as a cursor, and can be moved along the length of the two-dimensional graph via a user input. In this embodiment, the precise temporal coordinates corresponding to the cursor are displayed in a rectangular box 58 in the first rectangular portion 12a, and is also displayed at the upper left portion of the screen in FIG. 3. Moving the cursor along the length of the two-dimensional graph can also be used to navigate the data presented in the first rectangular portion 12a.

Figure 5:
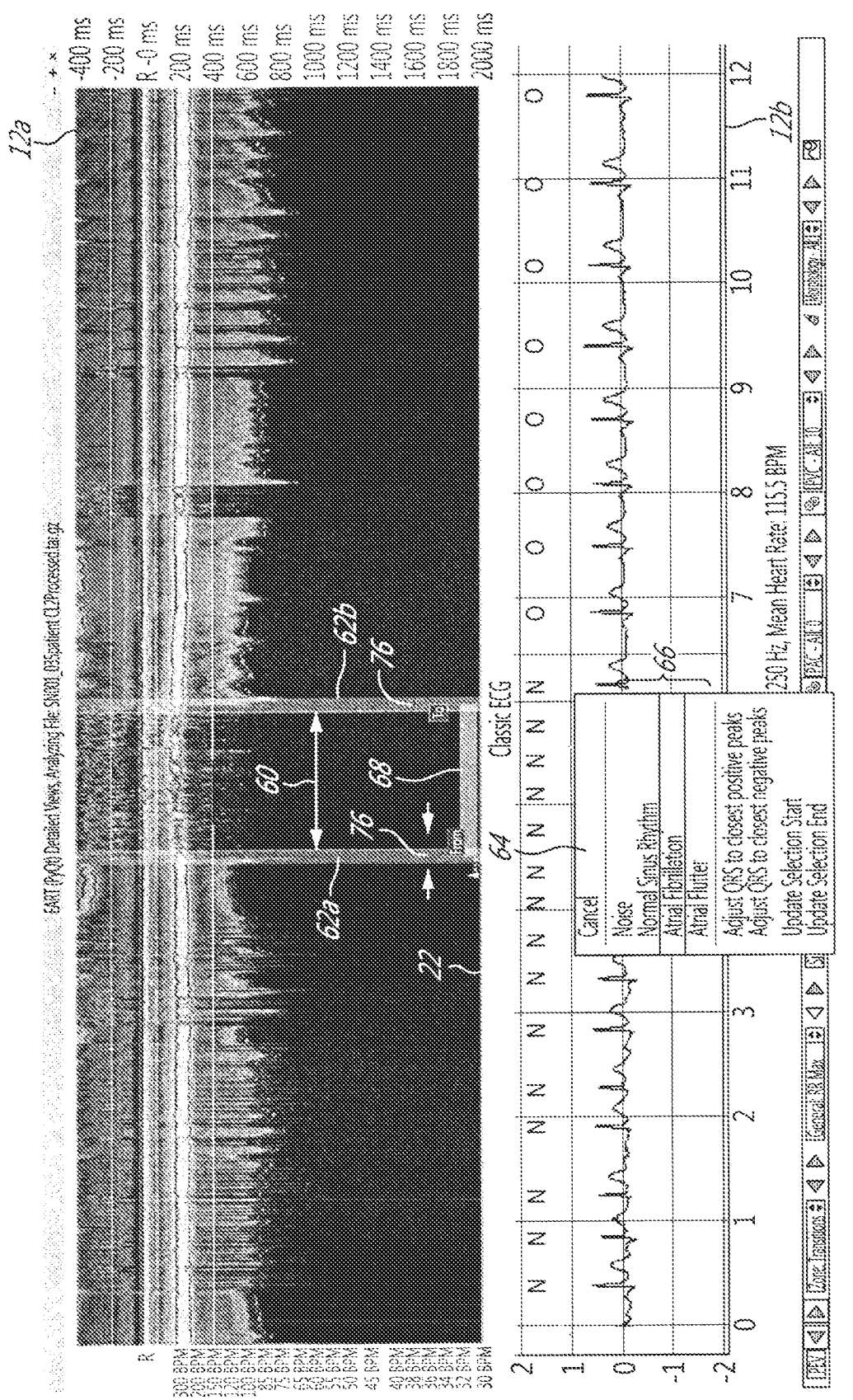
FIG. 5 shows an example of the categorization of a zone as atrial fibrillation.

Referring now to FIG. 5, a further function of categorizing a zone 60 of the electrocardiogram data will now be explored. Two variants will be considered, the first variant is a manual categorization of zones, and a second variant is an automatic categorization of zones.

As shown in FIG. 5, the computer can be used to categorize a zone 60 of the electrocardiogram data which is being displayed. This method can be used to categorize a zone 60 of electrocardiogram data being displayed with a series of unidimensional graphs, such as used in an upper rectangular portion 12a of the display screen of FIG. 5. Alternately, the method can be used to categorize a zone 60 of electrocardiogram data being displayed in a two dimensional graph, such as shown in a bottom rectangular portion 12b of the display screen of FIG. 5.

The method can include the computer receiving a first user input, and identifying a first temporal coordinate 62a of the electrocardiogram data based on the first user input. The first user input can be received by a user right-clicking, or touching, a given portion of the display screen to indicate spatial coordinates associated by the graphical representation to given temporal coordinates, for instance. Graphical feedback can be displayed in the form of a visual indicator, such as exemplified above. The method then include the computer receiving a second user input, and identifying a second temporal coordinate 62b of the electrocardiogram data based on the second user input. The computer can then define a zone 60 corresponding to a specific time interval of the electrocardiogram data as extending from the first temporal coordinate 62a to the second temporal coordinate 62b.

The definition of the zone 60 can be stored in a computer-readable memory by the computer. The computer can then receive a third user input to associate a category with the defined zone 60. Perhaps more specifically, the third user input is used to assign a category to the defined zone 60. For instance, the user can right-click between the two visual indicators to trigger a window 64 in which the user can select a given category among a plurality of possible categories 66. In the illustrated example, there are four possible categories 66: noise, normal sinus rhythm, atrial fibrillation (paroxysmal (PAF) or chronic (CAF)), atrial flutter, and the user selects atrial fibrillation. The category can be stored as data in association with the definition of the zone 60.

In this specific embodiment, the beginning of a selected zone 60, or "From" area, can automatically be adjusted by a user indicating a corresponding side of the displayed electrocardiogram data, outside the zone 60. For instance, the "From" area can automatically be moved by clicking on the left-hand side of the previously selected "From" area, and vice versa for the "To" area. To adjust the "From" area or the "To" area to a position within the selected zone 60, corresponding "update selection start" or "update selection end" functions can be selected from the pop-up window 64, as illustrated in FIG. 5.

In another variant, an application can be used to automatically detect categories of the electrocardiogram data, automatically define zones 60, and automatically assign corresponding categories 66 to corresponding zones 60. For instance, in the embodiment illustrated, an automatic noise identification algorithm is also performed on the electrocardiogram data prior to displaying the electrocardiogram data.

Alternately, automatic zone identification could be based on deep learning and/or an heart rhythm variability algorithm. For instance, a deep learning algorithm can be trained using data sets of formerly manually annotated ECG recordings. Such a deep learning algorithm could be used to automatically identify atrial fibrillation, atrial flutter, ectopic beats, AV blocks, bundle branch blocks and/or any other suitable form of arrythmia. For atrial fibrillation and atrial flutter, the deep learning identification could be refined using more classic heart rate variability algorithms, to more accurately identify the beginning and end of each zone or episode. The 2D color scale approach presented allows not only a highly compressed and expressive ECG representation for the technologists during their analysis task, but can further be better suited than traditional 2D graph data representation to allow deep learning algorithm to work on it as well.

One example of a noise identification algorithm executed after the QRS detection algorithm and can be summarized as follows:
  a high pass filter is applied to the resulting signal to remove the low frequency content typical of normal P and T waves;
  for each detected R-peak, a masking window is defined to encompass the QRS complex (i.e. from 50 ms prior to the R-peak to 100 ms following the R-peak);
  for each R-R interval, the algorithm computes the signal to noise ratio and compares the result to a threshold to determine if a given R-R interval will be identified as noise, with the threshold being set to a value at which the artifact content of a R-R interval becomes too high and prevents a technologist consulting the displayed electrocardiogram data from visually identifying a PQRST complex.

Zones 60 of the electrocardiogram data corresponding to specific time intervals where the signal is categorized as noise can be automatically defined by the computer, and the categories corresponding to these zones can be automatically stored in the memory in association with the definition of the zones.

In the embodiment illustrated in FIG. 5, a visual indicator 68, represented in the form of a horizontal bar extending along an edge 22 of the upper rectangular portion 12*a*, is used to indicate that a given zone 60 has been categorized. The category can be visually represented to the user by attributing a corresponding color to the horizontal bar, for instance. All the displayed electrocardiogram data in FIG. 3 has been categorized, and the categories are visually represented in this manner.

Figure 6:
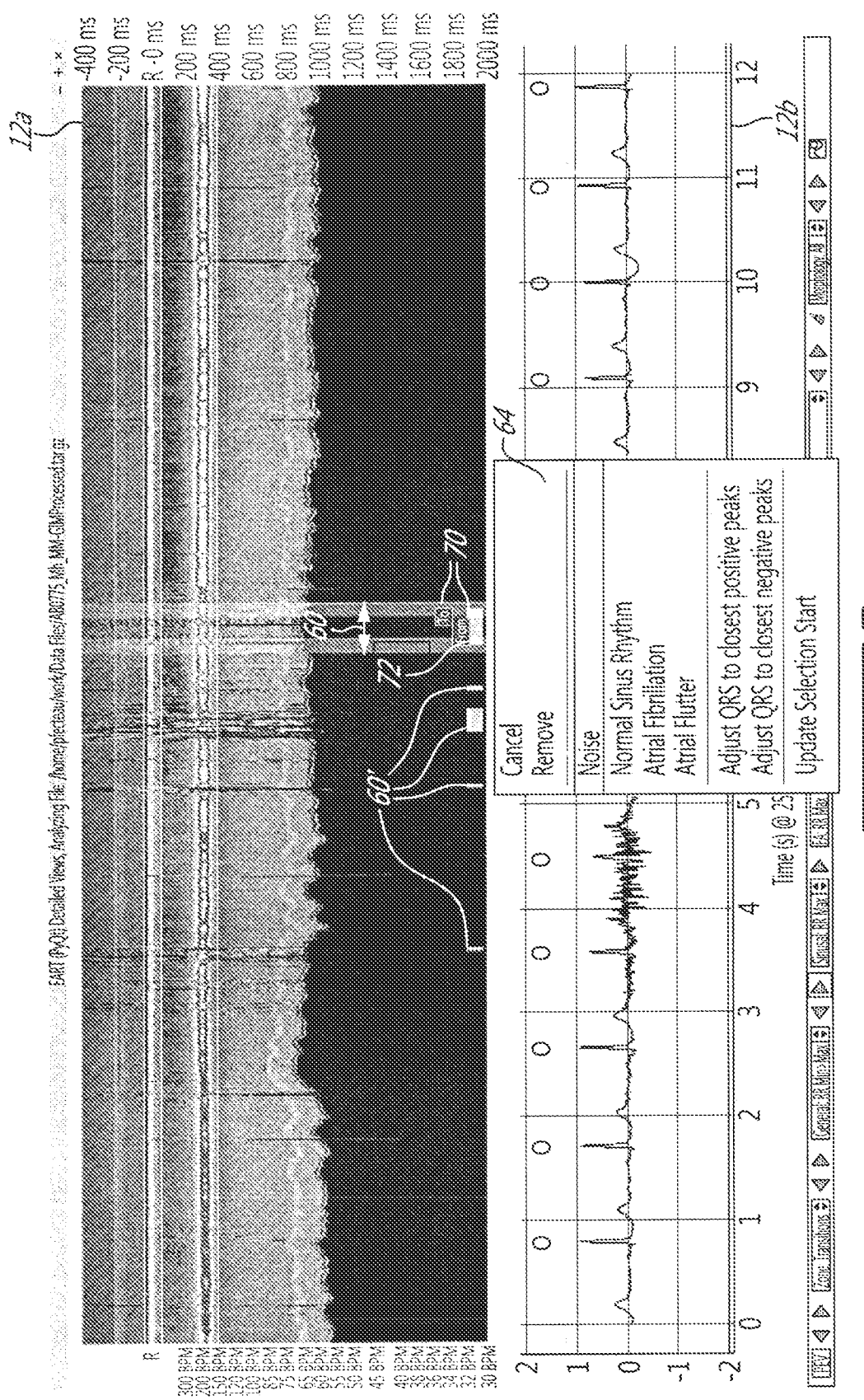
FIG. 6 shows several zones having been automatically categorized as noise, one of the noise zones being selected.

FIG. 6 shows zones 60' of the electrocardiogram data which have automatically been categorized by the software as noise. In the illustrated embodiment, the application provides the functionality of automatic zone selection: when the user indicates a given portion of the display which corresponds to a categorized zone 60, the zone 60 can be automatically selected, visual indicators 70 can be used to identify the beginning and the end of the zone, and a pop-up window 64 can be triggered to allow the user to remove the categorization of the zone 60, or to change the categorization of the zone 60, for instance. The automatic selection of the zone 60 can be triggered by clicking in the corresponding horizontal bar 72, for instance.

In the illustrated embodiment, the percentage of the overall electrocardiogram data (including both displayed and undisplayed portions thereof) which has been categorized is tracked. Moreover, in the display of FIG. 3, a progress bar 74 is used at an upper rectangular portion of the screen to visually indicate the percentage of the overall electrocardiogram data which has been categorized. Accordingly, in FIG. 3, 41% of the overall electrocardiogram data has been categorized, which immediately suggests to the user that portions of the electrocardiogram data which are not being currently displayed are uncategorized.

In the illustrated embodiment, the general workflow across which the application guides the skilled technician performing the categorization includes guiding the skilled technician to attribute a category to every portion of the overall electrocardiogram data, and thus to reach 100% on the progress bar 74. The application then generates a report (not illustrated) which summarizes the main features of the given collection of electrocardiogram data and which presents some excerpts of the electrocardiogram data, in the form of 2D graphs, which are representative of the given collection of electrocardiogram data. In the illustrated embodiment, the user is only given access to the report generation function once the 100% progress is reached, and thus cannot finalize the report as long as some portions of the electrocardiogram data are uncategorized. The report generation is contingent upon the full categorization of the electrocardiogram data.

The user can start by assessing the first 24*h* using a detailed view such as shown in FIG. 4 for instance, and then proceed with a quick overview of the remaining days using a main view such as shown in FIG. 3.

In this specific embodiment, the electrocardiogram data can be coded with patient events (PEV). For instance, patient event markers can be associated with temporal coordinates of the electrocardiogram data. The addition of patient event markers can be triggered by receiving a user input via the wearable monitor, during the recording of the electrocardiogram data, for instance. The CardioSTAT® device has a press button to this end. The application can provide a visual marker on the displayed electrocardiogram data at each PEV, or can be adapted to provide information concerning the PEVs in another manner. The user can be instructed to check for the presence of PEVs while linking it with notes in the patient logbook and/or abnormalities on the recording, for instance.

A snap-on feature is provided by the application software in order to avoid the occurrence of small gaps being involuntarily left between categorized zones of the electrocardiogram data. This snap-on feature will now be described.

The snap-on feature uses a predetermined time interval 76. When a zone "From" or "To" area is identified within the predetermined time interval 76 from an adjacent zone, the "From" or "To" area is automatically adjusted to coincide exactly with the corresponding end of the adjacent zone 60. The predetermined time interval 76 can be defined in units of time, or in units of heartbeats, for instance. In this example, the predetermined time interval 76 is defined in units of heartbeats. When the "From" or "To" selection is made by selecting coordinates in a compressed graph, such as shown in the upper rectangular portion 12a of FIG. 5 for instance, the predetermined time interval 76 can be set to a given number of heartbeats, such as 8 heartbeats, 10 heartbeats or 20 heartbeats for instance. When the "From" or "To" selection is made by selecting coordinates in a two-dimensional graph, such as shown in the lower rectangular portion 12b of FIG. 5 for instance, the software can infer that additional precision is intended by the user, and the predetermined time interval 76 can be lower, such as a single heartbeat for instance. Accordingly, if a user clicks an area in the compressed graph which corresponds to be within a predetermined time interval 76 of, say, 10 heartbeats of an adjacent zone 60, the corresponding end of the adjacent zone 60 can be automatically selected instead of the actual coordinates indicated by the user. This functionality can help avoid occurrences of small gaps between zones 60 which could otherwise be difficult to detect on a main view such as presented in FIG. 3.

Accordingly, when another zone is categorized prior to the step of categorizing a given zone 60, and if either one, or both, of the first temporal coordinate 62a and the second temporal coordinate 62b of the given zone 60 is adjacent to the first temporal coordinate and the second temporal coordinate of the other zone, within a buffer time interval, the corresponding one, or both, of the first temporal coordinate and the second temporal coordinate is identified as being the corresponding temporal coordinate of the other zone.

Meta zone categorization features can also be provided. A meta zone can be defined as a zone extending between a from (start) and a to (end) which spans across at least two sub-zones, the sub-zones either having different categories, or having at least one category and an uncategorized portion of the electrocardiogram data. For instance, when a meta zone is determined to have been defined a different pop-up menu can be presented to the user with additional functions. The menu can allow the user to attribute a given category to all uncategorized portions, remove the categorization of all zones having a given category, or remove all the categorization within the meta zone altogether, to name a few examples.

The software can have additional functions to those described above. For instance, additional automatic category recognition functions can be provided, such as PAC detection, PVC detection, and PVC morphology classification. In the illustrated embodiments, these additional algorithms are not used to automatically attribute a category go corresponding zones of the electrocardiogram data, but rather displayed as indicators destined to the attention of a skilled user of the software.

In the illustrated embodiment, a premature atrial contraction (PAC) detection algorithm is executed when a new ECG zone is annotated by the technologist as a normal zone. PAC are not physiologically applicable to atrial fibrillation or flutter zones and zones marked as noise, based on the above noise identification process, will also be excluded. The technologist has the ability to enable automatic PAC detection as well as defining the sensitivity of the PAC detection using a slider widget via the graphical user interface. An example of a PAC detection algorithm which can be enabled can be summarized as follows:

a list of detected QRS complex is first defined based on the user-categorized normal zone;

a sliding window applied from the first to the last QRS complex of the normal zone is then used as the R-R history leading to each QRS complex;

the last QRS complex of the sliding history window will be marked as a PAC if its R-R interval is lower than a threshold based on the R-R history leading to that QRS;

the threshold is parametrized so that the user can adjust it with a slider widget;

detected PAC can be annotated with the letter S in blue in an upper area of the two-dimensional graph view, and a short vertical red line can also be added to the bottom of the compressed graphical representation, such as shown in FIG. 4.

In the illustrated embodiment, a premature ventricular contraction (PVC) detection algorithm is executed when a new ECG zone is categorized by the technologist as a normal sinus rhythm, atrial fibrillation or flutter. Only zones marked as noise, based on the above noise identification process, will be excluded. The technologist has the ability to enable automatic PVC detection as well as defining the importance of the complex prematurity and the sensitivity of the PVC detection using two independent slider widgets from the graphical user Interface. When enabled, the PVC detection algorithm can be summarized as follows:

a list of detected QRS complexes is first defined based on the user delimited zone(s);

for each QRS complex of the list, the following 5 factors, each quantifying a specific characteristic of a PVC, are calculated:

complex prematurity which is quantified in a similar manner as for the PAC algorithm;

QRS complex width (Q-S interval), estimated based on the QRS complex morphology and normalized to the median width of all QRS falling within the selected zone(s)—PVC has typically larger QRS complex durations;

QRS complex amplitude, estimated using a subset of the QRS detection algorithm itself and also normalized using the median amplitude of all QRS falling within the selected zone(s);

QRS complex max value (which will typically be the amplitude of the positive R peak), also normalized using the median max value of all QRS falling within the selected zone(s);

QRS complex min value (which will typically be the amplitude of the negative S peak), also normalized using the median min value of all QRS falling within the selected zone(s);

a QRS complex will then be marked as a PVC if its prematurity is above a threshold proportional to the user defined prematurity slider widget value and the weighted sum of the other 4 factors is above the user defined PVC sensitivity slider widget value; and detected PVC can be annotated with the letter V in brown in an upper region of the two-dimensional graph view, and a short vertical red line can also be added at the bottom of the compressed graph, just below the space reserved for the PAC annotations.

In the illustrated embodiment, a PVC morphology classification algorithm is executed following the detection of new PVC. The technologist has the ability to define the sensitivity of the classification using a slider widget from the graphical user interface. The PVC morphology classification algorithm can be summarized as follows:

each detected but unclassified PVC morphology is compared with all previously classified PVC morphologies; the comparison is made by calculating the distance measure between the two PVC; a PVC will be considered similar to another PVC, hence in the same morphology family, if its distance measure is above an adjustable threshold defined by the morphology classification sensitivity slider widget value;

when an unclassified PVC does not meet the classification criterion of any previously classified PVC morphology, a new morphology family is created with this PVC as the first and only morphology; and PVC morphologies can be annotated with a family ID (e.g., a numerical value between 1 and 32) following the letter V on the two dimensional graph views.

As will be understood from the above, the technical tool presented herein can allow the user to visualize a large number of QRS complexes—in the tens of thousands—representing several hours of ECG recording in one static view. The number of QRS and the ECG duration which can be displayed in a single screen view vary depending on the heart rate of the recording and the screen resolution.

As will be understood from the above, the classic ECG recorded signal can be first divided into heartbeat segments, where one segment represents one beat to beat interval. In this example, the segments begin 400 ms before a given heartbeat and end at the detection point of the following heartbeat. In the color and/or tone scale, the isoelectric reference (0 mv) can be represented in yellow-green for instance, with the positive values from yellow-green through red then white (the warm colors) and the negative values from yellow-green through blue then black (the cold colors), although this is only one possible example. FIG. 4 shows an example of a detailed views where the compressed, color-coded graph in the upper rectangular portion corresponds to about 25 minutes of continuous ECG data and where the lower, two-dimensional graph, represents an ECG band of 12 seconds. In this view, the user can navigate through the ECG data recording by moving the yellow vertical cursor with a left mouse click in any of the three views. The cursor position will be updated to the new clicked position and the other two views will be re centered around the selected time point. Each view shows the navigation cursor and its position identifies the same time point in the ECG recording. At the bottom of the detailed view, a navigation tool bar allows the user to quickly synchronize the three ECG views onto a specific ECG event or arrhythmia.

The various functions presented above can be provided in the form of one or more computer program products (applications) stored in a memory readable by a computer.

As can be understood, the examples described above and illustrated are intended to be exemplary only. For instance, in alternate embodiments, the elongated rectangular portion can be oriented vertically rather than being oriented horizontally, and the contrasting margin can be presented above the graphs rather than below the graphs. The scope is indicated by the appended claims.

What is claimed is:

1. A computer-implemented method of handling electrocardiogram data having a plurality of magnitude values varying over time and representing a succession of heartbeats, the method comprising:
   the computer displaying the electrocardiogram data on a display; wherein the electrocardiogram data includes a plurality of single axis graphs
   the computer categorizing a first zone of the electrocardiogram data including:
      receiving a first user input and identifying a first temporal coordinate of the electrocardiogram data based on the first user input;
      receiving a second user input and identifying a second temporal coordinate of the electrocardiogram data based on a second user input;
      defining the first zone of the electrocardiogram data as extending between the first temporal coordinate and the second temporal coordinate; and
      receiving a third user input indicative of a category selected by a user on the computer, the computer assigning the category to the first zone based on the third user input.

2. The method of claim 1 wherein the first user input and the second user input are spatial coordinates of the displayed electrocardiogram data.

3. The method of claim 2 wherein a second zone is categorized prior to said step of categorizing a first zone, wherein when at least one of the first temporal coordinate of said first user input and the second temporal coordinate of said second user input is adjacent to a corresponding one of a first temporal coordinate and a second temporal coordinate of the second zone, within a buffer time interval, the corresponding at least one of the first temporal coordinate and the second temporal coordinate of the first zone is identified as being the corresponding temporal coordinate of the second zone.

4. The method of claim 3 wherein the buffer time interval is defined in terms of a quantity of heartbeats.

5. The method of claim 1 further comprising repeating the step of categorizing a first zone of the electrocardiogram data to the categorizing of other zones of the electrocardiogram data, the different zones each being attributed a corresponding category selected from a set of categories.

6. The method of claim 5 further comprising generating a report providing data concerning the attribution of categories, wherein said generating the report is contingent upon the condition that all portions of the electrocardiogram data have an attributed category.

7. The method of claim 5 further comprising tracking a percentage of the electrocardiogram data which has been attributed a category, and displaying a visual indication of the percentage on the display screen.

8. The method of claim 1 wherein the step of displaying the electrocardiogram data includes displaying the electrocardiogram data within at least one elongated rectangular portion of the display screen, with a plurality of single axis graphs extending transversally relative to the length of the at least one rectangular portion, and positioned immediately side by side to one another along the length of the at least one rectangular portion, each graph in the sequence representing a corresponding, successive, period of time of the electrocardiogram data with corresponding time values plotted as corresponding spatial coordinates along the single axis.

9. The method of claim 8 wherein the corresponding, successive period of time of the electrocardiogram data associated with each one of the graphs has magnitude values displayed by corresponding colors and/or tones as a function of a color and/or tone magnitude scale, the remaining area contrasting with the color and/or tone scale.

10. The method of claim 1 further comprising changing a displayed portion of electrocardiogram data to navigate to other portions of the electrocardiogram data based on user input.

11. The method of claim 1 further comprising displaying a first visual indicator marking the first temporal coordinate on the display screen, and a second visual indicator marking the second temporal coordinate on the display screen.

12. A computer program product stored in a computer memory and readable by the computer to perform the method according to claim 1.

\* \* \* \* \*